(12) United States Patent
Majewski et al.

(10) Patent No.: US 8,144,323 B2
(45) Date of Patent: Mar. 27, 2012

(54) APPARATUS, METHOD AND COMPUTER-READABLE STORAGE MEDIUM FOR DETERMINING THE RING-DOWN TIME IN A SPECTROMETER SYSTEM

(75) Inventors: Alexander Majewski, Fairfield, CT (US); Robert Noll, Fairfield, CT (US); Rene Abreu, The Villages, FL (US)

(73) Assignee: Goodrich Corporation, Charlotte, NC (US)

( * ) Notice: Subject to any disclaimer, the term of this patent is extended or adjusted under 35 U.S.C. 154(b) by 84 days.

(21) Appl. No.: 12/731,941

(22) Filed: Mar. 25, 2010

(65) Prior Publication Data

US 2011/0235022 A1    Sep. 29, 2011

(51) Int. Cl.
*G01J 3/28* (2006.01)
(52) U.S. Cl. ........................ 356/326; 356/317
(58) Field of Classification Search .............. 356/326, 356/437, 317, 440, 247, 432; 250/343, 344, 250/345, 339.13, 338.1; 372/29.01–32
See application file for complete search history.

(56) References Cited

U.S. PATENT DOCUMENTS

| | | | |
|---|---|---|---|
| 2,779,230 A | 1/1957 | White | |
| 5,267,019 A | 11/1993 | Whittaker et al. | |
| 5,818,578 A | 10/1998 | Inman et al. | |
| 5,883,518 A | 3/1999 | Borden | |
| 5,903,358 A | 5/1999 | Zare et al. | |
| 5,966,019 A | 10/1999 | Borden | |
| 6,348,683 B1 | 2/2002 | Verghese et al. | |
| 6,466,322 B1 | 10/2002 | Paldus et al. | |
| 6,486,474 B1 | 11/2002 | Owen et al. | |
| 6,500,618 B1 | 12/2002 | Woolard et al. | |
| 6,865,198 B2 | 3/2005 | Taubman | |
| 6,940,600 B1* | 9/2005 | Smith | 356/437 |
| 7,174,037 B2 | 2/2007 | Arnone et al. | |
| 7,271,594 B2 | 9/2007 | Abreu et al. | |
| 7,291,839 B1 | 11/2007 | Demers et al. | |
| 7,352,463 B2 | 4/2008 | Bounaix | |

(Continued)

FOREIGN PATENT DOCUMENTS

EP    2 166 324 A2    3/2010

(Continued)

OTHER PUBLICATIONS

Armerding, W. et al., *Multipass Optical Absorption Spectroscopy: a Fast-Scanning Laser Spectrometer for the in situ Determination of Atmospheric Trace-Gas Components*, in Particular OH, Applied optics, vol. 35, No. 21, (1996), pp. 4206-4219.

(Continued)

*Primary Examiner* — Tri T Ton
(74) *Attorney, Agent, or Firm* — Smith Moore Leatherwood LLP (57) ABSTRACT

A system is provided that includes a cavity ring-down spectrometer and a processor. The spectrometer is configured to pass, through a cavity resonator, a modulated, continuous-wave electromagnetic signal at each of one or more selectable, transmission frequencies in the Terahertz region of the electromagnetic spectrum. The spectrometer includes a transmitter that, with the cavity resonator, is configured so as to excite a single resonant mode of the cavity resonator. The processor is configured to receive a measurement of the passed portion of the modulated electromagnetic signal, and determine a phase shift of the modulated electromagnetic signal based upon the measurement. The processor is then configured to calculate a ring-down time of the cavity resonator as a function of the phase shift.

18 Claims, 2 Drawing Sheets

U.S. PATENT DOCUMENTS

| | | |
|---|---|---|
| 2002/0067480 A1 | 6/2002 | Takahashi |
| 2004/0114939 A1 | 6/2004 | Taylor |
| 2005/0201661 A1 | 9/2005 | Loock et al. |

FOREIGN PATENT DOCUMENTS

| | | |
|---|---|---|
| WO | WO 03/005510 A1 | 1/2003 |
| WO | WO 2004/083796 A1 | 9/2004 |

OTHER PUBLICATIONS

Auton, J. P., *Infrared Transmission Polarizers by Photolithography*, Applied Optics, vol. 6, No. 6, (1967), pp. 1023-1027.

Blickensderfer, R. P. et al., *A Long Path, Low Temperature Cell*, Applied Optics, vol. 7, No. 11, (1968), pp. 2214-2217.

Brown, E. R. et al., *Coherent Millimeter-Wave Generation by Heterodyne Conversion in Low-Temperature-Grown GaAs Photoconductors*, J. Appl. Phys., 73(3), (1993), pp. 1480-1484.

Edwards, T. H., *Multiple-Traverse Absorption Cell Design*, Journal of the Optical Society of America, vol. 51, No. 1, (1961), pp. 98-102.

Engel, G. S. et al., *Precise Multipass Herriott Cell Design: Derivation of Controlling Design Equations*, Optics Letters, vol. 32, No. 5, (2007), pp. 704-706.

Engeln, R. et al., *Phase Shift Cavity Ring Down Absorption Spectroscopy*, Chemical Physics Letters, 262, (1996), pp. 105-109.

Gregory, I. S. et al., *Resonant Dipole Antennas for Continuous-Wave Terahertz Photomixers*, [online] [retrieved May 24, 2010]. Retrieved from the Internet: <URL: http://adsabs.harvard.edu/abs/2004ApPhL..85.1622G>. 1 page.

Harmon, S. A. et al., *Part-Per-Million Gas Detection From Long-Baseline THz Spectroscopy*, Applied Physics Letters, vol. 85, No. 11, (2004), pp. 2128-2130.

Hayden, A. et al., *Determination of Trace-Gas Amounts in Plumes by the Use of Orthogonal Digital Filtering of Thermal-Emission Spectra*, Applied Optics, vol. 35, No. 16, (1996), pp. 2802-2809.

Herbelin, J. M. et al., *Sensitive Measurement of Photon Lifetime and True Reflectances in an Optical Cavity by a Phase-Shift Method*, Applied Optics, vol. 19, No. 1, (1980), pp. 144-147.

Lehmann, K. K. et al., *The Superposition Principle and Cavity Ring-Down Spectroscopy*; J. Chem. Phys., vol. 105, No. 23, (1996), pp. 10263-10277.

Mouret, G. et al., *THz Media Characterization by Means of Coherent Homodyne Detection, Results and Potential Applications*, Appl. Phys., B89, (2007), pp. 395-399.

Pickett, H. M. et al., *A New White Type Multiple Pass Absorption Cell*, Applied Optics, vol. 9, No. 10, (1970), pp. 2397-2398.

Rayl, G. J., *Multiple Traversal Absorption Cell of Minimum Volume: Design*, Applied Optics, vol. 15, No. 4, (1976), pp. 921-928.

Robert, C., *Simple, Stable, and Compact Multiple-Reflection Optical Cell for Very Long Optical Paths*, Applied Optics, vol. 46, No. 22, (2007), pp. 5408-5418.

Scherer, J. J. et al., *Cavity Ringdown Laser Absorption Spectroscopy: History, Development, and Application to Pulsed Molecular Beams*, Chem. Rev., 97, (1997), pp. 25-51.

Siegman, *11.5 Optical-Cavity Mode Frequencies*, Chapter 11: Laser Mirrors and Regenerative Feedback, pp. 435-437 (undated).

Verghese, S. et al., *Highly Tunable Fiber-Coupled Photomixers with Coherent Terahertz Output Power*, IEEE Transactions on Microwave Theory and Techniques, vol. 45, No. 8, (1997), pp. 1301-1309.

Verghese, S. et al., *Generation and Detection of Coherent Terahertz Waves Using Two Photomixers*, Applied Physics Letters, vol. 73, No. 26. (1998), pp. 3824-3826.

Verghese, S. et al., *The Photomixer Transceiver*, Invited Paper, SPIE Conference on Terahertz Spectroscopy and Applications, San Jose, CA, Jan. 1999, pp. 7-13.

White, J. U., *Very Long Optical Paths in Air*, J. Opt. Soc. Am., vol. 66, No. 5, (1976), pp. 411-416.

Zalicki, P. et al., *Cavity Ring-Down Spectroscopy for Quantitative Absorption Measurements*, J. Chem. Phys., 102 (7), (1995), pp. 2708-2717.

Extended European Search Report for European Patent Application No. 11250273.7, mailed Jul. 13, 2011.

Gopalsami, N., et al.; "Millimeter-wave cavity ringdown spectroscopy"; Review of Scientific Instruments; vol. 73; Issue 2; Feb. 2002; pp. 259-262.

Lewis, E.K., et al.; "Phase shift cavity ring-down measurement of C-H ($\Delta v = 6$) vibrational overtone absorptions"; Chemical Physics Letters; vol. 334; Issues 4-6; Feb. 2001; pp. 357-364.

Meshkov, A.I., et al.; "Broadband absolute absorption measurements of atmospheric continua with millimeter wave cavity ringdown spectroscopy"; Review of Scientific Instruments; vol. 76; Issue 8; Feb. 2005; 10 pages.

Romanini, D., et al.; "CW cavity ring down spectroscopy"; Chemical Physics Letters; vol. 264; Issue 304; Jan. 1997; pp. 316-322.

\* cited by examiner

APPARATUS, METHOD AND COMPUTER-READABLE STORAGE MEDIUM FOR DETERMINING THE RING-DOWN TIME IN A SPECTROMETER SYSTEM

FIELD OF THE INVENTION

Exemplary embodiments of present invention generally relate to spectrometer systems and methods of propagating electromagnetic signals and, more particularly, an apparatus, method and computer-readable storage medium for determining the ring-down time in a spectrometer system.

BACKGROUND OF THE INVENTION

The concept of a ring-down cavity to perform spectroscopy has been developed for application in the visible and infrared portions of the spectrum and discussed in the technical literature. Cavity ring-down (CRD) spectrometers may generally be one of two types, namely pulsed and continuous wave. In the pulsed case, a short pulse of light may be injected into a resonant cavity (often referred to as a cavity resonator or sample cell) which may include a pair of mirrors between which light may reflect. In spectrometer applications, the space between the mirrors in these cavities may be filled with a sample medium so that the absorption spectrum of the sample can be measured.

The mirrors may not be perfectly reflecting but may allow some light to pass through the mirrors for entrance and exit of the light. If a short single pulse is injected into an empty cavity, the pulse may reflect many times in the cavity, and on each encounter with an exit mirror, a pulse may exit the cavity. Thus, a single pulse may produce a train of pulses with each pulse subsequently reduced in pulse height as energy leaks out of the exit mirror on subsequent passes. The multiple reflections may be referred to as "ringing," and the time it takes the output pulse train to complete may be referred to as the "ring-down time." This time constant is a property of the cavity geometry and the medium between the reflecting mirrors. For more information on a pulsed ring-down cavity, see for example, K. Lehmannn & D. Romanini, *The Superposition Principle and Cavity Ring-Down Spectroscopy*, J. CHEM. PHYS., vol. 105 no. 23 (1996) (hereinafter "Lehmannn & Romanini"), the content of which is hereby incorporated by reference in its entirety.

SUMMARY OF THE INVENTION

In light of the foregoing background, embodiments of the present invention provide an improved apparatus, method and computer-readable storage medium for determining the ring-down time in a cavity ring-down (CRD) spectrometer system. According to one aspect of the present invention, a system is provided that includes a cavity ring-down spectrometer and a processor. The spectrometer includes a transmitter, modulator, cavity resonator and receiver. The transmitter, which may comprise a photomixer or terahertz or millimeter wave transmitter, is configured to transmit a continuous-wave electromagnetic signal at each of one or more selectable, transmission frequencies in the Terahertz region of the electromagnetic spectrum; and the modulator is configured to modulate (e.g., amplitude modulate) the electromagnetic signal at a modulation frequency.

The cavity resonator is configured to receive the modulated electromagnetic signal and pass at least a portion of the modulated electromagnetic signal. According to this aspect, the transmitter and cavity resonator are configured so as to excite a single resonant mode of the cavity resonator.

The receiver, which similar to the transmitter may comprise a photomixer or terahertz or millimeter wave receiver, is configured to receive the portion of the modulated electromagnetic signal passing the cavity resonator. The processor, in turn, is configured to receive a measurement of the portion of the modulated electromagnetic signal received by the receiver, and determine a phase shift of the modulated electromagnetic signal at the modulation frequency based upon the measurement. The processor is also configured to calculate a ring-down time of the cavity resonator as a function of the phase shift. And further, when the cavity resonator houses a sample medium, the processor may be configured to determine an absorption signature for the sample medium as a function of the ring-down time and transmission frequency.

In a more particular exemplary embodiment, the processor may be configured to calculate a ring-down time $\tau$ in accordance with the following:

$$\tan(\phi_{m'n'}) = 2\omega_{md}\tau$$

where $\phi_{m'n'}$ represents the phase shift at the modulation frequency for the single resonant mode m'n', and $\omega_{md}$ represents the modulation frequency. At terahertz frequencies, devices like the photomixer may offer the unique ability to measure not only the intensity but also the amplitude of radiation. Thus, the cavity resonator may have two ring-down times, one for the intensity and one for the amplitude which is twice the intensity ring-down time. In such instances, the aforementioned ring-down time may be considered the intensity ring-down time. The processor, then, may be additionally or alternatively configured to calculate an amplitude ring-down time $\tau_{amp}$ in accordance with the following:

$$\tan(\phi_{m'n'}) = \omega_{md}\tau_{amp}$$

According to other aspects of the present invention, a method and computer-readable storage medium are provided for determining the ring-down time in a spectrometer system. Exemplary embodiments of the present invention therefore provide an improved apparatus and method for determining the ring-down time in a spectrometer system. As explained below, exemplary embodiments of the present invention may solve problems identified by prior techniques and provide additional advantages.

BRIEF DESCRIPTION OF THE DRAWINGS

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In this regard, reference may be made herein to a number of mathematical or numerical expressions that may be related by equality. It should be understood, however, that this equality may refer to an absolute or approximate equality, such that exemplary embodiments of the present invention may account for variations that may occur in the system and method, such as those due to engineering tolerances. Further, although a number of variables may be reflected by mathematical symbols including subscripts at various instances, it should be understood that these symbols and subscripts are presented solely for illustrative purposes, and should not be construed as limiting the scope of the invention. Like numbers refer to like elements throughout.

Figure 1:
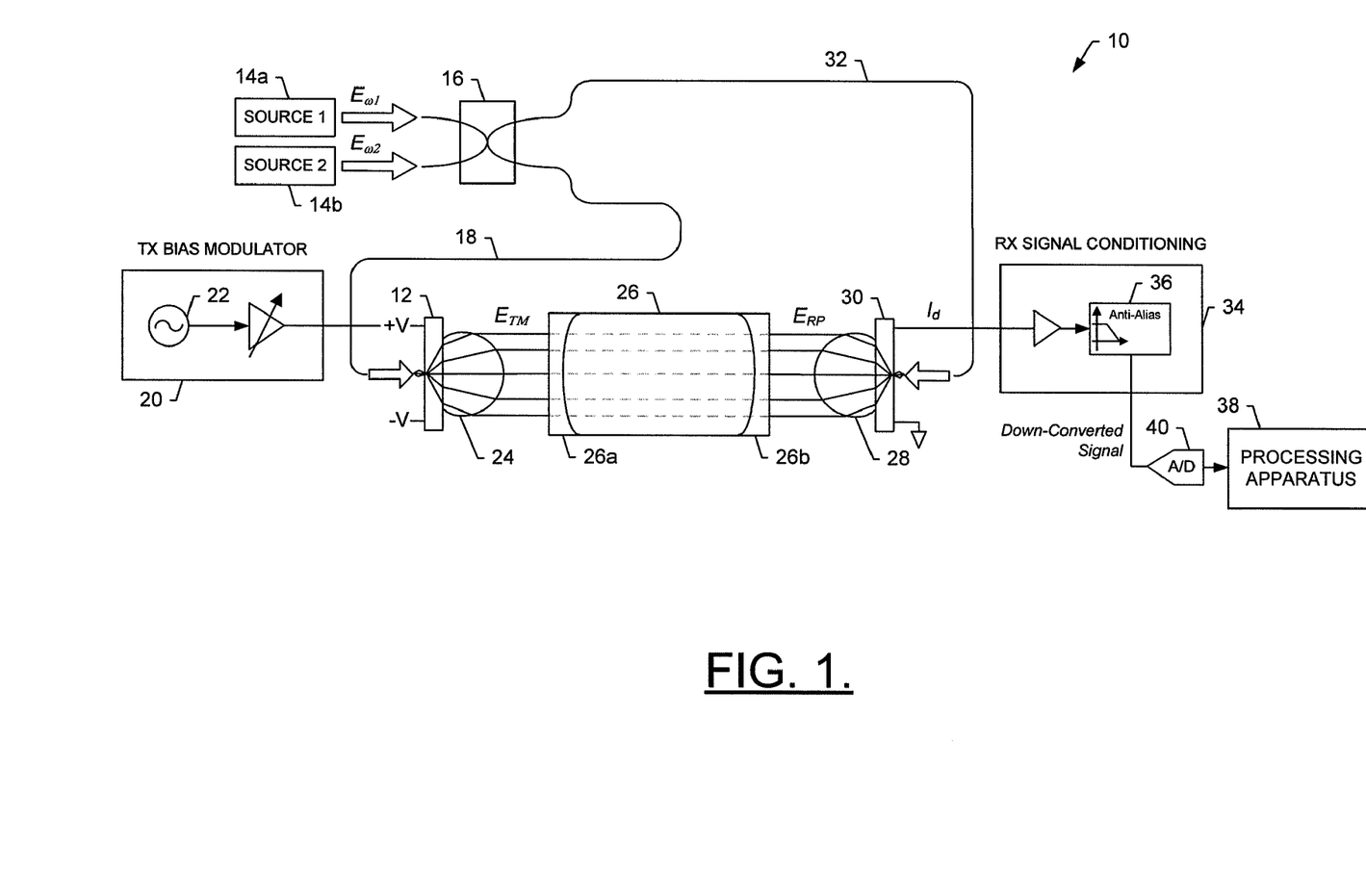
FIG. 1 is a schematic block diagram of a spectrometer system in accordance with one exemplary embodiment of the present invention.
Figure 2:
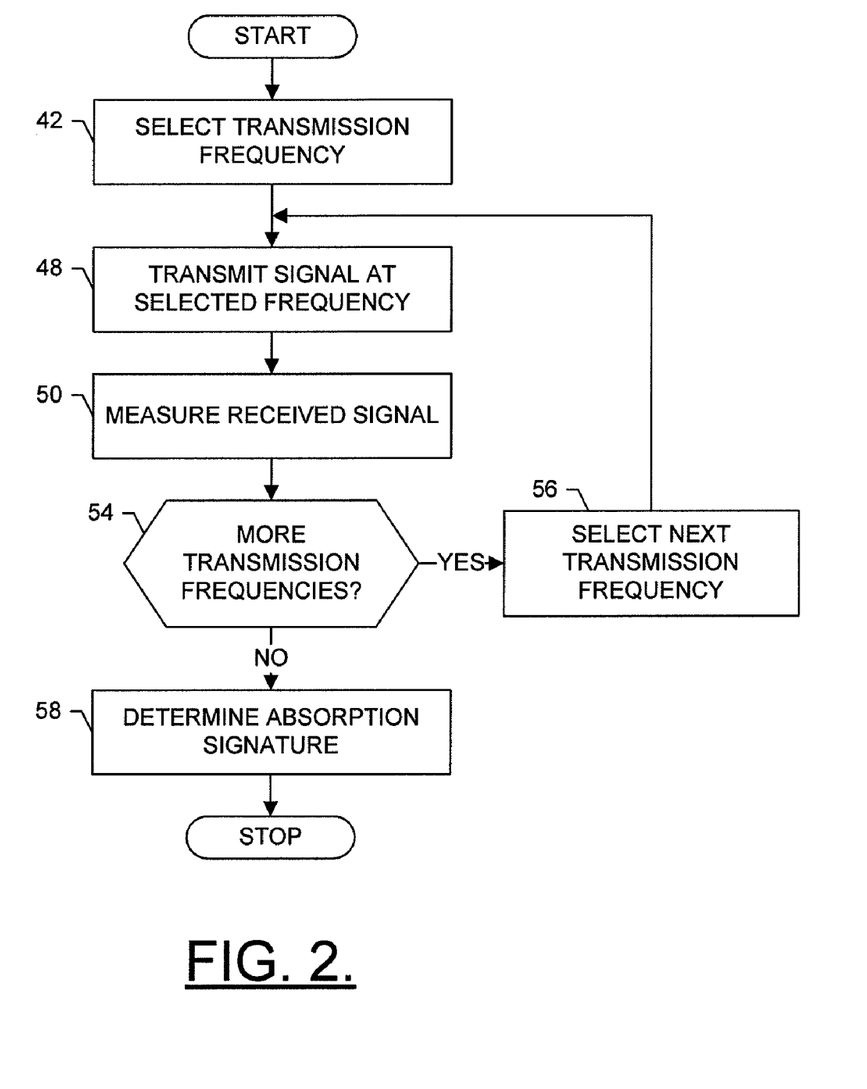
FIG. 2 is a flowchart illustrating various steps in a method of sweeping a spectrometer system through a frequency spectrum, according to exemplary embodiments of the present invention.

FIGS. 1 and 2 illustrate a spectrometer system and method that may benefit from exemplary embodiments of the present invention ("exemplary" as used herein referring to "serving as an example, instance or illustration"). It should be understood, however, that the spectrometer system and method illustrated and hereinafter described are merely illustrative of one type of system and method that may benefit from exemplary embodiments of the present invention and, therefore, should not be taken to limit the scope of the present invention. For an example of another spectrometer system and method that may benefit from exemplary embodiments of the present invention is described in U.S. patent application Ser. No. 12/712,736, entitled: System and Method for Magnitude and Phase Retrieval by Path Modulation, filed Feb. 25, 2010. The content of the '736 application is hereby incorporated by reference in its entirety.

While several embodiments of the spectrometer system and method are illustrated and will be hereinafter described for purposes of example, other types of systems and methods of propagating electromagnetic signals may readily employ the present invention. Moreover, the system and method of the present invention will be primarily described in conjunction with signals in the THz (or mmW) region of the electromagnetic spectrum. But the system and method of embodiments of the present invention may be utilized in conjunction with a variety of other applications, both within and outside the THz region of the electromagnetic spectrum.

As shown, a spectrometer system 10 of one exemplary embodiment of the present invention includes a transmitter 12 configured to transmit a beam of coherent radiation (electromagnetic wave) at a given frequency. The transmitter can comprise any of a number of different transmitters known to those skilled in the art. In one exemplary embodiment, for example, the transmitter comprises a photomixer transmitter. In such instances, the transmitter includes a high-speed photoconductive diode (i.e., photomixer), which may be pumped with two laser sources 14a, 14b via a beam combiner/splitter 16 and an optically coupled first optical path 18 (e.g., optical fiber). In this regard, the laser sources may be configured to emit signals with electric fields having offsetting frequencies at $\omega_1$ and $\omega_2$ (i.e., $E_{\omega 1}$ and $E_{\omega 2}$). Also note that frequencies $\omega_1$ and $\omega_2$, and other frequencies described herein, may be expressed as radian angular frequencies, or as corresponding temporal frequencies ($f=\omega/2\pi$).

The transmitter 12 may be coupled to a transmitter bias modulator 20 including a voltage source 22 configured to generate a sinusoidal modulated voltage with which the photomixer of the transmitter may be biased, the modulator producing an electric field $E_M=V_m \cos(\omega_{md} t)$, thereby amplitude modulating the transmitted signal at frequency $\omega_{md}$. By locating the photomixer at the driving point of an antenna, such as a spiral, dipole or slot antenna, the difference-frequency current is converted to difference-frequency photons. The result is a highly-tunable, continuous-wave (CW), highly-coherent source of radiation contained in a single (quasi-Gaussian) spatial mode, and having a transmitted electric field $E_{TM}$. For more information on such a transmitter, see U.S. Pat. No. 6,348,683 entitled: Quasi-Optical Transceiver Having an Antenna with Time Varying Voltage, issued Feb. 19, 2002.

Thus, the method of one exemplary embodiment includes selecting a transmission frequency, thereafter transmitting a beam of radiation (i.e., source beam) at that frequency from the transmitter 12, as shown in blocks 42 and 48 of FIG. 2. The transmission frequency can be selected in any of a number of different manners. To detect a sample based upon a measured absorption signature, however, the transmission frequency may be typically selected within a range of frequencies over which the absorption signature is defined. In a photomixer transmitter, then, the photomixer can be pumped with tunable laser sources at a frequency $\omega_2$, and a frequency $\omega_1$ that are selected to thereby select the difference, or transmission, frequency (e.g., $\omega_2-\omega_1$).

The beam of radiation from the transmitter 12 may pass through a collimating lens 24 to produce a collimated beam of radiation. The beam may then pass through a cavity resonator 26 or sample cell that may be bounded by reflectors 26a and 26b through which the beam passes, and that may include a sample medium to be analyzed and a base medium, such as ambient air. As will be appreciated, the sample and base medium can have any of a number of different forms through which the beam of radiation is at least partially transmissive. For example, the sample and base medium can comprise a solid, liquid, gas, plasma or aerosol. More particularly, in various advantageous embodiments, the base medium of ambient air may be in gas form, while a sample may be in gas or aerosol form.

The cavity resonator 26 may have an actuator control to vary the length between the reflectors 26a and 26b, which may permit changing the frequency sampling comb and thereby lend flexibility to the system by providing continuous tuning across an entire desired spectral range. The reflectors of the cavity resonator may be configured to have a high reflectivity, such as on the order of 0.995–0.998 for certain THz bands. The reflectors 26a and 26b may be configured in any of a number of different manners to achieve a desired reflectivity and optical function. In one example embodiment, the reflectors may include a gold grating polarizer coating. For a further discussion of suitable coatings, see J. Auton, *Infrared Transmission Polarizers by Photolithography*, APPLIED OPTICS, vol. 6, no. 6 (1967); and R. Ulrich et al., *Variable Metal Mesh Coupler for Far Infrared Lasers*, APPLIED OPTICS, vol. 9, no. 11, (1970).

As the continuous-wave beam of radiation is introduced to the cavity resonator 26, its intensity builds up as the beam reflects between the reflectors 26a and 26b. But as the beam reflects between the reflectors, the sample and base medium in the cavity resonator absorb at least a portion of the beam, or more particularly at least a portion of the electric field of the beam; and a remaining, unabsorbed portion of the beam of radiation (i.e., received signal) then exits the cavity resonator. The sample signal then propagates to a focusing lens 28, from which the focused signal is picked up or otherwise received by a receiver 30 as a received signal $E_{RP}$.

The receiver obtains a measurement representative of the received electric field $E_{RP}$. Similar to the transmitter 12, the receiver may comprise an electric-field detector such as a photomixer receiver (homodyne receiver). The photomixer receiver may include an antenna configured to receive the electric field and generate a corresponding voltage in response thereto, which may be directed to a high-speed photoconductor. The photoconductor is also electrically coupled to a second optical path 32 for pumping the photoconductor with beams from the same two laser sources 14a, 14b pumping the photomixer transmitter 12. In this regard, the beam combiner/splitter 16 may separate each of the signals from the laser sources into the aforementioned first optical path 18, as well as another, second optical path (e.g., optical fiber) for pumping the receiver photomixer. These signals, then, may modulate a conductance of the photomixer.

The voltage generated by the receiver antenna may be applied to the photomixer active material, and produce a current through the modulated conductance. The difference frequency result of the product is the down-converted signal current $I_d$, which may have a corresponding down-converted electric-field $E_R$, either or both of which may constitute or otherwise represent a signal. For more information on such a receiver, see the aforementioned '683 patent.

The down-converted signal current $I_d$ and/or electric-field $E_R$ may be applied to receiver signal conditioning circuitry 34 including, for example, an anti-aliasing filter 36. The output of the signal conditioning circuitry may then be input to a processing apparatus 38, such as for performing digital signal processing operations thereon. In this regard, the processing apparatus can comprise any of a number of different devices capable of operating in accordance with exemplary embodiments of the present invention. For example, the processing apparatus may comprise a computer (e.g., personal computer, laptop computer, server computer, workstation computer) or other computing apparatus. The processing apparatus may include a processor and computer-readable storage medium. The processor may include, for example, one or more programmed or programmable general-purpose processors, microprocessors, coprocessors, controllers, specialized digital signal processors and/or various other processing devices including one or more integrated circuits (e.g., ASICs, FPGAs), hardware accelerators, processing circuitry or the like.

The computer-readable storage medium of the processing apparatus 38 may include volatile and/or non-volatile memory, which may be embedded and/or removable, and may include, for example, read-only memory, flash memory, magnetic storage devices (e.g., hard disks, floppy disk drives, magnetic tape, etc.), optical disc drives and/or media, non-volatile random access memory (NVRAM), and/or the like. The computer-readable storage medium may store any of a number of different data, content or the like, according to exemplary embodiments of the present invention. For example, the computer-readable storage medium may be configured to store executable or other computer-readable instructions that may be executed or otherwise processed by the processor.

When the spectrometer system 10 frequency modulates the signal, the signal processing operations performed by the processor 38 may include recovering the amplitude of the down-converted signal $E_R$ such as by an analog-to-digital converter (A/D) 40 direct sampling of the signal at the modulating frequency, and the processor Discrete Fourier Transformation (DFT) processing of the sampled data. Alternatively, for example, the spectrometer system may further include a synchronous demodulator such as a lock-in amplifier (not shown) for further processing the down-converted signal $E_R$. In this regard, such a synchronous demodulator may include a local oscillator operating at the modulating frequency $\omega_{md}$ to thereby recover the amplitude of the down-converted signal.

In operation as a continuous wave CRD spectrometer, the sample signal exiting the cavity resonator 26 may be monitored until it reaches a particular threshold intensity, the transmitter 12 may be shut-off or otherwise controlled to cease transmission of the beam into the cavity resonator. In this regard, the shut-off switch may be configured such that its falling-edge is short compared to the ring-down time of the excited modes. With the transmitter ceasing transmission of the beam into the cavity resonator, the intensity of the beam propagating within the cavity resonator, and thus the portion of the beam exiting the cavity resonator, decays exponentially (i.e., "rings down") until no more of the beam exits the cavity resonator or the exiting portion of the beam becomes immeasurable. The time between the transmitter ceasing transmission of the beam into the cavity resonator and the last of the beam exiting the cavity resonator (or the last of the exiting beam being measurable), then, may be measured as the "ring-down time," as shown in block 50 of FIG. 2. The ring-down time may be measured in a number of different manners, one of which is more particularly described below.

The system 10 scans through a number of transmission frequencies in a range of frequencies, such as by pumping the photomixers of the transmitter 12 and receiver 30 with tunable laser sources at frequency $\omega_2$, and frequency $\omega_1$ that are scanned through a number of frequencies, as shown in blocks 54 and 56. For each transmission frequency in the range of frequency, and thus each beam of radiation having a different transmission frequency, the processor 38 may measure or otherwise determine the ring-down time τ. The resulting collection of ring-down times, and associated transmission frequencies, may be used to determine absorption or dispersion signature for the sample in the cavity resonator 26, from which the sample may be identified, as shown in block 58 of FIG. 2. For example, an absorption or dispersion signature may be determined by plotting cavity loss (1/cτ, where c represents the speed of light) as a function of transmission frequency.

By implementing a phase shift cavity ring-down technique, many of the typical problems of spectroscopic characterization and detection may be avoided. Again, in the ring-down method, a beam of radiation may be injected into the cavity resonator 26 as an amplitude modulated carrier. The cavity resonator presents a delay to the traveling wave, which may introduce a phase shift (delay) for both the carrier and modulated (envelope) waves. The presence of an absorber changes the intrinsic cavity decay time and presents a different delay. This can be measured in two ways: a decay time or through a phase shift at the modulation frequency (see FIG. 2, block 50). By measuring delay times or phase shifts, issues associated with energy normalization may be reduced over the pulsed method, if not obviated.

The analysis of Lehmannn & Romanini shows that each transverse cavity mode m, n has an exponential decay (ring-down time) $t_d$ that may be expressed—for intensity measurements—as follows:

$$t_{d,mn}(\omega_{mnq}) = \frac{t_r R_{mn,eff}}{2(1 - R_{mn,eff})} \quad (1)$$

In the preceding, $R_{mn, eff} = R_{mn} \exp(-\kappa(\omega_{mnq})L)$, with $R_{mn}$ representing the modal reflectivity of the cavity reflectors 26a, 26b (the mode dependence of the reflectivity comes from the coefficient of the input field expanded in terms of the cavity modes). Also, L represents the cavity length, $t_r$ represents the round trip travel time of light in a single cycle, $\omega_{mnq}$ represents the angular frequency of the m, n transverse and q longitudinal modes of the cavity resonator 26, and κ represents the absorption coefficient of the sample medium in the cavity. Given the following assumptions with c representing the speed of light: $t_r/2=L/c$, $\kappa L \ll 1$; $R_{mn} \sim R_{0,0} \sim 1$; and $\tau = t_{d,00}$ ($\omega_{0,0,q}$), the intensity ring-down time at longitudinal frequency $v_q$ may be given by:

$$\tau(v_q) = \frac{L}{c[(1 - R_{0,0}) + \kappa(v_q)L]}$$

Lehmannn & Romanini point out that if $R_{mn}$ is not constant due to mode dependent loss, the ring-down time may have a non-exponential dependence with or with out a sample medium in the cavity resonator. They also indicate for the pulsed case, the input pulse should have a falling edge less than the decay time of the excited longitudinal mode.

Unlike the pulsed case of Lehmannn & Romanini where the input pulse width may be short and the frequency spectrum may be wide, a continuous wave (CW) case may have a long time span and an impulse frequency input. The modulated CW case may lead to a cavity response that, in the observed signal, produces a phase shift that is related to the ring-down time. In this case, a modulated input beam may emerge from the cavity resonator 26 shifted in phase go (at the modulation frequency $f_{md}$), and with a corresponding intensity ring-down time, which may be given by:

$$\tan(\phi) = 4\pi f_{md} \tau \quad (2)$$

In accordance with example embodiments of the present invention, a measurement of the ring-down time may be achieved when the input continuous wave beam is modulated. Thus, when the input beam to the cavity is modulated with an angular frequency $\omega_{md}$, the ring-down time may be measured in terms of a phase shift of the modulated continuous wave current. This may be done by representing the cavity input field in terms of the cavity resonant modes which may be assumed to be the Hermite-Gaussian modes. The analytic 2-dimensional modal transfer function may then be calculated and used to determine the output field coefficients from the input field coefficients. This transfer function may include both the effects of the transverse and longitudinal modes.

Consider a cavity resonator 26 including reflectors 26a and 26b that have an identical or substantially-identical radius of curvature $R_c$, amplitude transmittance T and reflectance R. Assuming a monochromatic beam of radiation and a sinusoidal modulation of that beam, the analysis may begin by describing the relationship between a cavity input ($c^i$) and output ($c^o$) transverse mode coefficients of the input and output fields, and the cavity mode transfer function $G_{mn}$, all evaluated at some temporal frequency $f = \omega/2\pi$. This relationship may be expressed as follows (cf. Lehmannn & Romanini, equation (26)):

$$c_{mn}^o(\omega) = G_{mn}(\omega) c_{mn}^i(\omega) \quad (3)$$

where the cavity mode transfer function $G_{mn}$ may be as provided by equation (27) in Lehmannn & Romanini.

For the modulated input beam coefficients, the coefficients may be taken as $$c_{mn}^i(\omega) = \pi c_{mn}[\delta(\omega - (\omega_0 - \omega_{md})) + \delta(\omega - (\omega_0 - \omega_{md}))] \quad (4)$$

where $\delta$ represents the standard mathematical delta function, $c_{mn}$ represents the transverse mode coefficients of the input field, and $\omega_0$ represents the CW transmission frequency (e.g., ($\omega_2 - \omega_1$)). Given the cavity mode transfer function $G_{mn}$ may, then, the output field coefficients $c_{mn}^o$ may be found from equations (3) and (4); and together with an expression for the total output field (e.g., Lehmannn & Romanini, equation (31)), the output field coefficients may provide an expression for the output field $E_R$ in the time domain.

When the receiver 30 is an electric-field (or amplitude) detector such as a photomixer receiver (homodyne receiver) that collects the entire output field, this spatially integrated field may be viewed as a current at the receiver and may be expressed as the following complex function (i representing the imaginary unit):

$$I_d(t) = 0.5 \sum_{m,n} K_{m,n}(\omega_0) F_m(\omega_0) F_n(\omega_0) \quad (5)$$

$$c_{m,n} \left[ \frac{T^2 \exp(i\omega_{md}(t - 0.5 t_r))}{1 - R_{mn,eff} \exp(-i(\omega_0 - \omega_{l'} + \omega_{md})t_r + i\delta k_{m,n} 2L)} + \frac{T^2 \exp(-i\omega_{md}(t - 0.5 t_r))}{1 - R_{mn,eff} \exp(-i(\omega_0 - \omega_{l'} + \omega_{md})t_r + i\delta k_{m,n} 2L)} \right]$$

In the preceding, $K_{m,n}$ represents mode constants such as those given in equation (21) of Lehmannn & Romanini evaluated at the output face of the cavity resonator 26, $F_m$ and $F_n$ each represent a component of the 2-dimensional integral of each cavity mode, and $\omega_{l'}$ represents radian longitudinal mode frequency of the cavity resonator closest to the transmission frequency $\omega_0$. Also in the preceding, $\delta k_{m,n}$ describes the transverse m, n modes defined by $$\delta k_{m,n} L = 2(m + n + 1) \tan^{-1}\left(\sqrt{\frac{L}{2R_c - L}}\right)$$

The function $F_m$ (and similarly $F_n$) may be notationally expressed by the integrated amplitude modes as follows:

$$F_m(\omega_0) = \int_{-\infty}^{\infty} dx H_m\left(\frac{\sqrt{2} x}{w(L/2)}\right) \exp\left(-\left(\frac{1}{w^2(L/2)} - \frac{ik}{2R_w(L/2)}\right)x^2\right)$$

where $H_m$ represents the mth Hermite-Gaussian amplitude mode, $w(L/2)$ represents the Gaussian beam waist at the output reflector 26b, and $R_w(L/2)$ represents the beam radius of curvature at the output reflector. And further to the above, k represents the wave vector of the beam of radiation, and may be expressed as:

$$k = \frac{2\pi}{\text{wavelength}}; \quad k = n_{cav} \frac{\omega_0}{c}$$

where $n_{cav}$ represents the complex refractive index of the sample medium between the reflectors.

Equation (5) may be simplified if the following substitutions are made:

$$R_{mn,eff} = \rho_{mn} e^{i\theta_{mn}}; \quad \phi_{mn}^t = \delta k_{mn} 2L; \quad \phi = \omega_{md} t_r \quad (7)$$

$$y_{mn} = (\omega_0 - \omega_{l'})t_r - \phi_{mn}^t - \theta$$

$$coef_{mn} = \frac{T^2 K_{m,n}(\omega_0) F_m(\omega_0) F_n(\omega_0) c_{m,n}}{(1 - \rho_{mn} \exp(-i(y_{mn} + \phi)))(1 - \rho_{mn} \exp(-i(y_{mn} - \phi)))}$$

To get $$I_d(t) = \sum_{mn} coef_{m,n}[\cos(\omega_{md}t - 0.5\phi) - \rho_{mn}e^{-iy_{mn}}\cos(\omega_{md}t + 0.5\phi)] \quad (8)$$

The variable $\rho_{mn}$ represents the modal reflectivity of the cavity reflectors 26a, 26b, $\theta_{mn}$ represents a phase shift associated with reflection, and $y_{mn}$ represents a dummy variable that collects phase shifts due to misalignment of the transmission frequency $\omega_0$ from a cavity longitudinal mode, phase shifts of the mode itself and/or phase shifts associated with the mirrors of the cavity. Further, the complex variable $coef_{mn}$ represents a dummy variable that collects some of the parts in equation (5) to permit rewriting equation (5) in the desired form of equation (8).

Defining the amplitude of the current at the receiver 30 as $A_{mn}e^{iq_{mn}}=coef_{mn}$ gives the following complex demodulated signal:

$$I_d(t) = \quad (9)$$
$$\sum_{mn} A_{m,n}[\cos(\omega_{md}t - 0.5\phi)e^{iq_{mn}} - \rho_{mn}e^{-i(q_{mn}-y_{mn})}\cos(\omega_{md}t + 0.5\phi)]$$

where $q_{mn}$ represents the entire phase of the complex variable $coef_{mn}$ ($q_{mn}$ representing the imaginary part of the natural log of the complex variable $coef_{mn}$). As $coef_{mn}$ depends on $\phi$, it may be seen that $q_{mn}$ depends on $\phi$; and consequently, $q_{mn}$ depends on the ring-down time.

Converting $I_d(t)$ to a real signal using $I(t)=2\,\mathrm{Re}(I_d(t))$ and trigonometric identities yields the sinusoidal signal sum:

$$I_d(t) = 2\sum_{m,n} A_{mn}r_{mn}\cos(\omega_{md}t - \varphi_{mn}) \quad (10)$$

where, $$r_{mn}^2 = 2(\cos^2(q_{mn}) + \rho_{mn}^2\cos^2(q_{mn} - y_{mn})), \text{ and}$$

$$\tan(\varphi_{mn}) = \frac{(\cos(q_{mn}) + \rho_{mn}\cos(q_{mn} - y_{mn}))\sin(0.5\phi)}{(\cos(q_{mn}) - \rho_{mn}\cos(q_{mn} - y_{mn}))\sin(0.5\phi)} \quad (11)$$

In the preceding, $\phi_{mn}$ represents a phase shift of the current at the receiver 30 (shifted from the frequency-modulated, input signal). The variable $r_{mn}$ represents a real number that contributes only to the amplitude in equation (10); it does not depend on time or the phase of the cosine.

When the transmission frequency $\omega_0$ is on a particular l', m', n' cavity resonance mode, $y_{m'n'}=0$; and when $q_{m'n'}=0$ (i.e., $coef_{mn}$ is real), equation (11) simplifies to:

$$\tan(\varphi_{m'n'}) = \frac{1 + \rho_{m'n'}}{1 - \rho_{m'n'}}\tan(0.5\phi) \approx \frac{\omega_{md}t_r}{1 - \rho_{m'n'}} \quad (12)$$

For small $\phi$ and $\rho_{m'n'}$ close to unity, the last part of equation (12) shows how the phase shift of the demodulated current $\phi_{m'n'}$ is related to the ring-down time of the cavity through $t_r$ and equation (2) may be recovered using the—intensity—ring-down time from equation (1) written as:

$$\tau = \frac{t_r\rho_{m'n'}}{2(1 - \rho_{m'n'})}$$

The $\rho$ in the numerator may be set to one when the reflectors 26a, 26b are highly reflecting; and thus, substituting the above expression into equation (12) may yield equation (2):

$$\tan(\phi_{m'n'})=\tan(\phi)=2\omega_{md}\tau=4\pi f_{md}\tau \quad (13)$$

At THz frequencies, a photomixer receiver 30 may offer the unique ability to measure not only the intensity but also the amplitude of radiation. Thus, the cavity resonator 26 may have two ring-down times, one for the intensity and one for the amplitude which is twice the intensity ring-down time. In terms of the amplitude ring-down time, $\tau_{amp}$ equation (13) may be expressed as follows:

$$\tan(\phi_{m'n'})=\tan(\phi)=\omega_{md}\tau_{amp}=2\pi f_{md}\tau_{amp} \quad (14)$$

When the m'n' mode is the only cavity mode excited by the input beam, then measuring the phase in equation (13) may provide a measure of the ring-down time of the cavity as defined in equation (13). Given all the conditions used to arrive at equation (13) from equation (11), it may be seen that equation (13) is a particular result of the more general equation (11), which also relates $\omega_{mn}$ to the intensity decay time $\tau$.

$$\tan(\varphi_{mn}) = \frac{(\cos(q_{mn}(\tau)) + \rho_{mn}\cos(q_{mn}(\tau) - y_{mn}))}{(\cos(q_{mn}(\tau)) - \rho_{mn}\cos(q_{mn}(\tau) - y_{mn}))}\tan\left(\frac{\omega_{md}(1 - \rho_{mn})\tau}{\rho_{mn}}\right) \quad (15)$$

In implementation, the expression equation (15) may be desired for increased accuracy. In such instances, a calibration of the instrument could determine the coefficient of the tangent on the right side of equation (15) as a short polynomial in $\tau$, but it may require the processing apparatus 38 to invert equation (15). The choice of using either equation (13) or (15) may therefore rest on the desired performance requirements imposed on the system spectrometer 10. It may be expected that in most cases of interest, however, equation (15) provides only minor modifications to equation (13). The fact that the phase in equation (13) may be measured means that, as long as the phase of the cosinusoid is measured, the result is nearly independent of the amplitude.

It should be noted that when the demodulation contains degenerate transverse modes, the sum in equation (10) may not contain just one term; and each term in the sum may contribute a phase factor adding to the phase noise in the system. It may therefore be beneficial to excite a single cavity mode for ring-down measurements. Single mode cavity excitation requirements may demand care in source beam spatial filtering and frequency control. These can be accomplished, for example, with well established beam alignment and filtering methods using narrow-band spectral sources derived in a variety of ways that include phase-lock loop frequency references and up-conversion by diode multipliers. On the other hand, there are two ways in which several cavity modes may be excited, and for which it may be desirable to avoid. The first is with a monochromatic input source and a degenerate cavity such as confocal cavity resonator; and the second is with a quasi-monochromatic source whose linewidth spans multiple cavity modes. In the second case, each mode may be excited in proportion to the input energy of the source at the different mode frequencies. In addition, the current at the receiver 30 may see phase noise associated with the linewidth of the source. In the first case, the confocal cavity may produce degenerate transverse modes of the sort labeled above by the m, n indices. Because of this degeneracy, several spatial modes may have the same frequency as the longitudinal mode so their selection may depend on mode shape overlap with the input profile. Moving the cavity away from confocal, may remove the degeneracy and provide a more robust selection by frequency discrimination.

According to one aspect of the example embodiments of present invention, the operations performed by the processing apparatus 38, such as those illustrated by the block diagram of FIG. 3, may be performed by various means. It will be understood that each block or operation of the block diagram, and/or combinations of blocks or operations in the block diagram, can be implemented by various means. Means for implementing the blocks or operations of the block diagram, combinations of the blocks or operations in the block diagram, or other functionality of example embodiments of the present invention described herein may include hardware, and/or a computer program product including a computer-readable storage medium having one or more computer program code instructions, program instructions, or executable computer-readable program code instructions stored therein. In this regard, program code instructions may be stored on a computer-readable storage medium and executed by a processor, such as those of the processing apparatus.

As will be appreciated, program code instructions may be loaded onto a computer or other programmable apparatus (e.g., processor, memory, or the like) from a computer-readable storage medium to produce a particular machine, such that the particular machine becomes a means for implementing the operations specified in the block diagram's block(s) or operation(s). These program code instructions may also be stored in a computer-readable storage medium that can direct a computer, a processor, or other programmable apparatus to function in a particular manner to thereby generate a particular machine or particular article of manufacture. The instructions stored in the computer-readable storage medium may produce an article of manufacture, where the article of manufacture becomes a means for implementing the functions specified in the block diagram's block(s) or operation(s). The program code instructions may be retrieved from a computer-readable storage medium and loaded into a computer, processor, or other programmable apparatus to configure the computer, processor, or other programmable apparatus to execute operations to be performed on or by the computer, processor, or other programmable apparatus. Retrieval, loading, and execution of the program code instructions may be performed sequentially such that one instruction is retrieved, loaded, and executed at a time. In some example embodiments, retrieval, loading and/or execution may be performed in parallel such that multiple instructions are retrieved, loaded, and/or executed together. Execution of the program code instructions may produce a computer-implemented process such that the instructions executed by the computer, processor, or other programmable apparatus provide operations for implementing the functions specified in the block diagram's block(s) or operation(s).

Accordingly, execution of instructions associated with the blocks or operations of the block diagram by a processor, or storage of instructions associated with the blocks or operations of the block diagram in a computer-readable storage medium, supports combinations of operations for performing the specified functions. It will also be understood that one or more blocks or operations of the block diagram, and combinations of blocks or operations in the block diagram, may be implemented by special purpose hardware-based computer systems and/or processors which perform the specified functions, or combinations of special purpose hardware and program code instructions.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A system comprising:
    a cavity ring-down spectrometer comprising:
        a transmitter configured to transmit a continuous-wave electromagnetic signal at each of one or more selectable, transmission frequencies in the Terahertz region of the electromagnetic spectrum;
        a modulator configured to modulate the electromagnetic signal at a modulation frequency;
        a cavity resonator configured to receive the modulated electromagnetic signal and pass at least a portion of the modulated electromagnetic signal, wherein the transmitter and cavity resonator are configured so as to excite a single resonant mode of the cavity resonator; and
        a receiver configured to receive the portion of the modulated electromagnetic signal passing the cavity resonator; and
    a processor configured to receive a measurement of the portion of the modulated electromagnetic signal received by the receiver, and determine a phase shift of the modulated electromagnetic signal at the modulation frequency based upon the measurement, and wherein the processor is configured to calculate a ring-down time of the cavity resonator as a function of the phase shift.

2. The system of claim 1, wherein the processor being configured to calculate a ring-down time includes being configured to calculate an intensity ring-down time $\tau$ in accordance with the following:

$$\tan(\phi_{m'n'}) = 2\omega_{md}\tau$$

wherein $\phi_{m'n'}$ represents the phase shift at the modulation frequency for the single resonant mode m'n', and $\omega_{md}$ represents the modulation frequency.

3. The system of claim 1, wherein the processor being configured to calculate a ring-down time includes being configured to calculate an amplitude ring-down time $\tau_{amp}$ in accordance with the following:

$$\tan(\phi_{m'n'}) = \omega_{md}\tau_{amp}$$

wherein $\phi_{m'n'}$ represents the phase shift at the modulation frequency for the single resonant mode m'n', and $\omega_{md}$ represents the modulation frequency.

4. The system of claim 1, wherein the cavity resonator is configured to house a sample, and
    wherein the processor is configured to determine an absorption signature for the sample medium as a function of the ring-down time and transmission frequency.

5. The system of claim 1, wherein the transmitter comprises a photomixer transmitter, and the receiver comprises a photomixer receiver.

6. The system of claim 1, wherein the transmitter comprises a terahertz or millimeter wave transmitter, and the receiver comprises a terahertz or millimeter wave receiver.

7. A method comprising:
- transmitting a continuous-wave electromagnetic signal at each of one or more selectable, transmission frequencies in the Terahertz region of the electromagnetic spectrum, the electromagnetic signal being transmitted from a transmitter in a cavity ring-down spectrometer;
- modulating the electromagnetic signal at a modulation frequency;
- passing at least a portion of the modulated electromagnetic signal through a cavity resonator, wherein the transmitter and cavity resonator are configured so as to excite a single resonant mode of the cavity resonator;
- receiving a measurement of the portion of the modulated electromagnetic signal passing the cavity resonator;
- determining a phase shift of the modulated electromagnetic signal at the modulation frequency based upon the measurement; and
- calculating a ring-down time of the cavity resonator as a function of the phase shift.

8. The method of claim 7, wherein calculating a ring-down time comprises calculating an intensity ring-down time $\tau$ in accordance with the following:

$$\tan(\phi_{m'n'}) = 2\omega_{md}\tau$$

wherein $\phi_{m'n'}$ represents the phase shift at the modulation frequency for the single resonant mode m'n', and $\omega_{md}$ represents the modulation frequency.

9. The method of claim 7, wherein calculating a ring-down time comprises calculating an amplitude ring-down time $\tau_{amp}$ in accordance with the following:

$$\tan(\phi_{m'n'}) = \omega_{md}\tau_{amp}$$

wherein $\phi_{m'n'}$ represents the phase shift at the modulation frequency for the single resonant mode m'n', and $\omega_{md}$ represents the modulation frequency.

10. The method of claim 7, wherein the cavity resonator houses a sample, and
- wherein the method further comprises determining an absorption signature for the sample medium as a function of the ring-down time and transmission frequency.

11. The method of claim 7, wherein transmitting a continuous-wave electromagnetic signal comprises transmitting a continuous-wave electromagnetic signal from a photomixer transmitter, and wherein receiving a measurement comprises receiving a measurement from a photomixer receiver.

12. The method of claim 7, wherein transmitting a continuous-wave electromagnetic signal comprises transmitting a continuous-wave electromagnetic signal from a terahertz or millimeter wave transmitter, and wherein receiving a measurement comprises receiving a measurement from a terahertz or millimeter wave receiver.

13. A non-transitory computer-readable storage medium having computer-readable program code portions stored therein, the computer-readable program portions comprising:
- a first executable portion configured to receive a measurement, the measurement having been received from a spectrometer system configured to:
  - transmit a continuous-wave electromagnetic signal at each of one or more selectable, transmission frequencies in the Terahertz region of the electromagnetic spectrum, the electromagnetic signal being transmitted from a transmitter in a cavity ring-down spectrometer;
  - modulate the electromagnetic signal at a modulation frequency; and
  - pass at least a portion of the modulated electromagnetic signal through a cavity resonator, wherein the transmitter and cavity resonator are configured so as to excite a single resonant mode of the cavity resonator, the measurement comprising a measurement of the portion of the modulated electromagnetic signal passing the cavity resonator;
- a second executable portion configured to determine a phase shift of the modulated electromagnetic signal at the modulation frequency based upon the measurement; and
- a third executable portion configured to calculate a ring-down time of the cavity resonator as a function of the phase shift.

14. The computer-readable storage medium of claim 13, wherein the third executable portion being configured to calculate a ring-down time includes being configured to calculate an intensity ring-down time $\tau$ in accordance with the following:

$$\tan(\phi_{m'n'}) = 2\omega_{md}\tau$$

wherein $\phi_{m'n'}$ represents the phase shift at the modulation frequency for the single resonant mode m'n', and $\omega_{md}$ represents the modulation frequency.

15. The computer-readable storage medium of claim 13, wherein the third executable portion being configured to calculate a ring-down time includes being configured to calculate an amplitude ring-down time $\tau_{amp}$ in accordance with the following:

$$\tan(\phi_{m'n'}) = 2\omega_{md}\tau$$

wherein $\phi_{m'n'}$ represents the phase shift at the modulation frequency for the single resonant mode m'n', and $\omega_{md}$ represents the modulation frequency.

16. The computer-readable storage medium of claim 13, wherein the cavity resonator houses a sample, and
- wherein the computer-readable program portions further comprise a fourth executable portion configured to determine an absorption signature for the sample medium as a function of the ring-down time and transmission frequency.

17. The computer-readable storage medium of claim 13, wherein the spectrometer system being configured to transmit a continuous-wave electromagnetic signal includes being configured to transmit a continuous-wave electromagnetic signal from a photomixer transmitter, and wherein the spectrometer system being configured to receive a measurement includes being configured to receive a measurement from a photomixer receiver.

18. The computer-readable storage medium of claim 13, wherein the spectrometer system being configured to transmit a continuous-wave electromagnetic signal includes being configured to transmit a continuous-wave electromagnetic signal from a terahertz or millimeter wave transmitter, and wherein the spectrometer system being configured to receive a measurement includes being configured to receive a measurement from a terahertz or millimeter wave receiver.

* * * * *